United States Patent [19]

Ruch et al.

[11] Patent Number: 5,747,031
[45] Date of Patent: May 5, 1998

[54] PROCESS FOR ISOLATING IMMUNOGLOBULINS IN WHEY

[75] Inventors: Frank E. Ruch, Falmouth; Elizabeth A. Acker, New Gloucester, both of Me.

[73] Assignee: ImmuCell Corporation, Portland, Mass.

[21] Appl. No.: 539,539

[22] Filed: Oct. 5, 1995

[51] Int. Cl.$^6$ .......................... A61K 39/42; A61K 39/40; A61K 39/395; C07K 16/00

[52] U.S. Cl. ...................... 424/130.1; 424/147.1; 424/150.1; 424/151.1; 424/157.1; 530/387.1; 530/386

[58] Field of Search ............... 424/130.1, 147.1, 424/150.1, 151.1, 157.1

[56] References Cited

PUBLICATIONS

Hwang, et al: Selective precipitation and removal of lipids from cheese whey using chitosan: J. of Food Chem.: 43: pp. 33–37, 1995.

Bokhout, et al.: Porcine IgG isolation of two IgG–subclasses and anti–IgG class–and subclass–specific antibodies: Molecular Immunology: V. 23, No. 6: pp. 675–683, 1986.

Harlow, et al. Antibodies a laboratory manual: p. 300, 1988.

Bokhout, et al.: Porcine IgG isolation of two . . . : Mol. Imm.. :vol. 23, No. 6: pp. 675–683, 1986.

*Primary Examiner*—Lynette F. Smith
*Assistant Examiner*—Brett Nelson
*Attorney, Agent, or Firm*—Kevin M. Farrell

[57] ABSTRACT

The present invention is directed to a process of isolating immunoglobulins from whey or whey concentrate and a concentrated immunoglobulin product which is highly purified. The process features the co-precipitation of lipids and non-immunoglobulin proteins simultaneously with a charged polymer and a fatty acid.

14 Claims, 1 Drawing Sheet

PROCESS FOR ISOLATING IMMUNOGLOBULINS IN WHEY

FIELD OF THE INVENTION

The present invention is directed to a process of isolating immunoglobulins from whey and whey concentrate, and a concentrated immunoglobulin product which is highly purified and readily administered.

BACKGROUND OF THE INVENTION

Immunoglobulins or antibodies are made by higher animals in response to the presence of a foreign composition. Such a foreign composition, capable of eliciting an immune response, is referred to as an antigen. Immunoglobulins are complex proteins which are capable of specifically binding or attaching to the antigen.

Immunoglobulins play an important role in a host organism's fight against disease. Immunoglobulins, often abbreviated as Ig, or antibodies abbreviated Ab, are made in several different forms. These classes of immunoglobulin are IgG, which is abundant in internal body fluids and certain lacteal secretions; IgA, abundant in sero-mucous secretions; IgM, an effective agglutinator; IgD, found on the surface of lymphocytes; and IgE, involved in allergic responses. IgG is the principle immunoglobulin in bovine milk and colostrum, while IgA is the dominant immunoglobulin in lacteal secretions in humans. The level of antigen specific immunoglobulins present in milk or colostrum can be increased through parenteral or intra mammary immunization regimes.

Hyperimmune immunoglobulins derived from bovine milk or colostrum have been proposed for use in a variety of pharmaceutical/medicinal applications. Among these are oral and topical applications for the treatment or prevention of infections diseases caused by pathogens including C. parvum, rotavirus, H. pylori, E. coli, Shigella species, S. mutans and Candida species. Immunoglobulins for this purpose can be from colostrum, which is the first 4-5 milkings after calving, or from milk produced during the remainder of the lactation. While immunoglobulins are present in relatively high concentrations (20-100 mg/ml) in colostrum compared to milk (0.3-0.5 mg/ml), production of commercial quantities of immunoglobulins from colostrum is made difficult both by limited supplies and the complexities of collecting and processing small volumes from individual cows on a commercial scale. Milk in contrast, is in abundant supply and has well established systems for collection and processing. While immunoglobulin levels in milk are low, it is well known that the majority of milk immunoglobulins pass into whey during conventional cheese making. Whey is a low cost and abundant byproduct of the cheese making industry and is readily available as a raw material for Ig purification. In addition to the relatively low concentrations of immunoglobulins in milk and whey, the other difficulty in producing commercial quantities of purified whey immunoglobulins is the presence of high concentrations (4-6 mg/ml) of non-immunoglobulin proteins including B-lactoglobulin and α-lactalbumin. Removal of greater than 90% of these proteins is required to produce a final product in which immunoglobulins constitute greater than 60% of the total protein. Production of commercial quantities of Ig's from whey, therefore, requires processing methods which allow for convenient and low cost removal of non-immunoglobulin proteins and high-throughput of large liquid volumes.

SUMMARY OF THE INVENTION

The present invention features a method for purifying immunoglobulins from whey which provides a final whey protein preparation that is greater than 60% by weight immunoglobulins. One embodiment of the present invention features a method of isolating immunoglobulins from concentrated whey derived from milk-bearing mammals vaccinated with an antigen. The method comprises forming an admixture of pasteurized whey concentrate, a charged polymer and a fatty acid. The admixture has a pH, temperature and salt concentration. The charged polymer is added to a concentration at which it is soluble in the admixture, and upon imposition of precipitation conditions the charged polymer forms a lipid-polymer precipitate and a liquid phase. The fatty acid is represented by the formula:

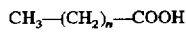

where n is a whole number from 4-10. The fatty acid is added at a concentration and temperature at which the fatty acid is soluble and upon imposition of precipitation conditions the fatty acid forms a protein precipitate and a liquid phase. The method further comprises the step of imposing precipitation conditions to form a protein precipitate, a lipid precipitate and a liquid phase. The liquid phase is separated from the protein and lipid precipitates. This liquid phase is rich in immunoglobulins and can be further processed.

Surprisingly and unexpectedly, the combination of a cationic polymer and a fatty acid allows simultaneous precipitation of non-immunoglobulin proteins and lipids. The remaining eluant is >60% immunoglobulin. Such a purity is comparable with the concentration of immunoglobulins present in colostral whey.

The lipid precipitates and protein precipitates can be separated simultaneously by a relatively low speed centrifugation (6–12,000×g) to produce a clear supernatant having a high concentration of immunoglobulins. The supernatant can be further concentrated and diafiltered to produce a composition which is greater than 70% immunoglobulin protein and 0.1% lipid by dry weight. This supernatant can be dried.

Preferably, the fatty acid and cationic charged polymer are selected to have precipitation conditions which are similar.

Preferably, the cationic charged polymer is a selected from the group comprising polypeptides and charged polysaccharides. A preferred charged polysaccharide is chitosan. Chitosan is a cationic polymer derived from partially deacetylated chitin.

Chitosan forms a gel-like complex with polar lipids at a pH of 4.5–5.0.

Preferably, in the formula:

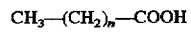

n is 6; that is, the fatty acid is caprylic acid. Caprylic acid forms colloid-like aggregates with non-immunoglobulin proteins at a pH of 4.5–5.0.

In the situation where the cationic polysaccharide comprises chitosan, conditions for forming a lipid precipitate comprise a pH of 4.5–5.0, a temperature of 20°–250° C. and a concentration of chitosan of 0.05 to 0.3% by weight volume. In the situation where the fatty acid is caprylic acid, conditions for forming a protein precipitate comprise a pH of 4.5–5.0, a temperature of 20°–25° C. and a concentration of caprylic acid of 1.0 to 5.0% by volume. The coprecipitation of lipids and protein requires only one step and requires fewer reagents than separate steps. Indeed, surprisingly and unexpectedly, the chitosan-lipid precipitate aids in the removal of the fatty acid-protein precipitate is which by itself requires either lengthy high speed (>15,000×g) centrifugation or microfiltration for effective removal of the submicron size particulates. Only low speed centrifugation is necessary for the removal of the combined precipitates.

Preferably, the Ig rich supernatant is concentrated by ultrafiltration to remove low molecular weight protein and peptides, forming a further Ig enriched retentate. Preferably, ultrafiltration is performed with a membrane having molecular weight cutoff of about 10,000 to 150,000 Daltons, and, more preferably 20,000 to 50,000 Daltons.

Preferably, the Ig rich retentate is further concentrated by diafiltration to remove peptides, minerals and lactose, to form a dialyzed immunoglobulin concentrate. A preferred dialysis filtration buffer is a potassium citrate buffer of pH 6.5.

The immunoglobulin containing supernatant is preferably processed by sterile filtration. Sterile filtration is difficult with materials which have high lipid concentrations.

The sterile filtrate is dried to form a dried immunoglobulin rich product.

Preferably, the dialysized Ig concentrate is freeze dried to form a powder. The dried immunoglobulin product has an improved shelf life since high lipid levels are a major factor in dry product spoilage. The dried immunoglobulin products produced by the present method have less than 6.0% lipid.

Embodiments of the present invention are capable of using whey derived from pasteurized cheese whey. Cheese whey is pasteurized at 151° to 159° F. for 15 to 17 seconds.

Preferably, the concentrated whey of the first admixture is made by ultrafiltering pasteurized whey. Preferably, ultrafiltration is performed with a membrane having a 20,000–150,000 Dalton molecular weight cut-off and, most preferably, a 30,000 Dalton molecular weight cut-off.

Concentrated whey of the first admixture may be prepared by either spiral membrane or hollow fiber ultrafiltration of pasteurized whey. Preferably, hollow fiber ultrafiltration is used with membranes having a molecular weight cut off of 20,000 to 150,000 Daltons and, most preferably, 30,000 Daltons. A preferred hollow fiber ultrafiltration membrane is a polysulfone hollow fiber membrane. This membrane produces a concentration factor of 5–10 fold.

Preferably, the concentrated whey is further subjected to ion exchange chromatography to reduce the concentration of non-immunoglobulin proteins. A preferred chromatographic ion exchange process uses a strong anionic resin and whey protein concentrate having a pH of 6.5–7.0. Anion exchange chromatography under these conditions can be used to remove from 20–70% of non-immunoglobulin proteins from whey or whey protein concentrate without significantly altering immunoglobulin levels. Partially deproteinized whey or whey protein concentrates are a preferred starting material for whey immunoglobulin purification by the combined precipitation process described above. Because of reduced non-immunoglobulin protein levels and smaller processing volumes, reduced amounts of complexing agents are therefore required with this starting material.

A further embodiment of the present invention features an immunoglobulin product derived from concentrated whey from milk bearing mammals hyperimmunized with an antigen to produce immunoglobulins of interest. The immunoglobulin product comprises at least 60% by weight volume antibody, <5% lipid, and <20% non Ig proteins. This product can be further processed to remove water to produce an Ig product comprising at least 70% antibody, less than or equal to 6.0% lipid and less than 20% non-Ig protein which can be administered for the treatment of disease.

Preferably, the immunoglobulin products comprise antibodies capable of binding antigens from one or more pathogenic organisms. Such pathogenic organism is preferably selected from one or more of the group consisting of *Cryptosporidium parvum*, Rotavirus, *Shigella flexneri*, *Heliobacter pylori*, *Clostridium difficile*, *Vibrio cholerae*, *Streptococcus mutans*, Candida species and enterotoxigenic *Escherichria coli*.

The immunoglobulin product of the present invention can be administered to subjects as a reconstituted liquid, tablet, capsule, granules or food bar. Due to the removal of non-immunoglobulin proteins and lipids, an effective dose of immunoglobulin can be administered readily in a variety of formats.

Embodiments of the present invention are capable of simultaneously removing the residual lipids, cheese culture bacteria, denatured protein aggregates and fatty acid precipitated whey protein. Lipid and protein precipitates can be removed by relatively low speed centrifugation in the presence of the chitosan. The simultaneous centrifugation of the protein precipitates with the lipid precipitates improved the recovery of highly purified immunoglobulins.

Protein and lipid precipitates are not readily removed by conventional microfiltration methods without also reducing the recovery of immunoglobulins because of the submicron size of much of the fatty acid protein precipitation. Although the concentration of lipid in separated whey is low, as whey is concentrated for processing, residual lipids reach levels of 5–20% dry weight.

These high lipid concentrations compromise the processing as well as the storage of liquid Ig products. Products with high levels of lipids cannot be sterile filtered and are subject to spoilage. These problems are overcome with the present process.

Products made in accordance with the present process feature low lipid and low non-Ig protein content. Such immunoglobulin enriched products occupy a small volume and weight for an effective dosage. Ig fractions which comprise the product can be sterile filtered and have a longer shelf life.

These and other features will become apparent from the drawings and the detailed description which follows, which, by way of example, without limitation, describe preferred embodiments of the present invention.

DETAILED DESCRIPTION

Figure 1:
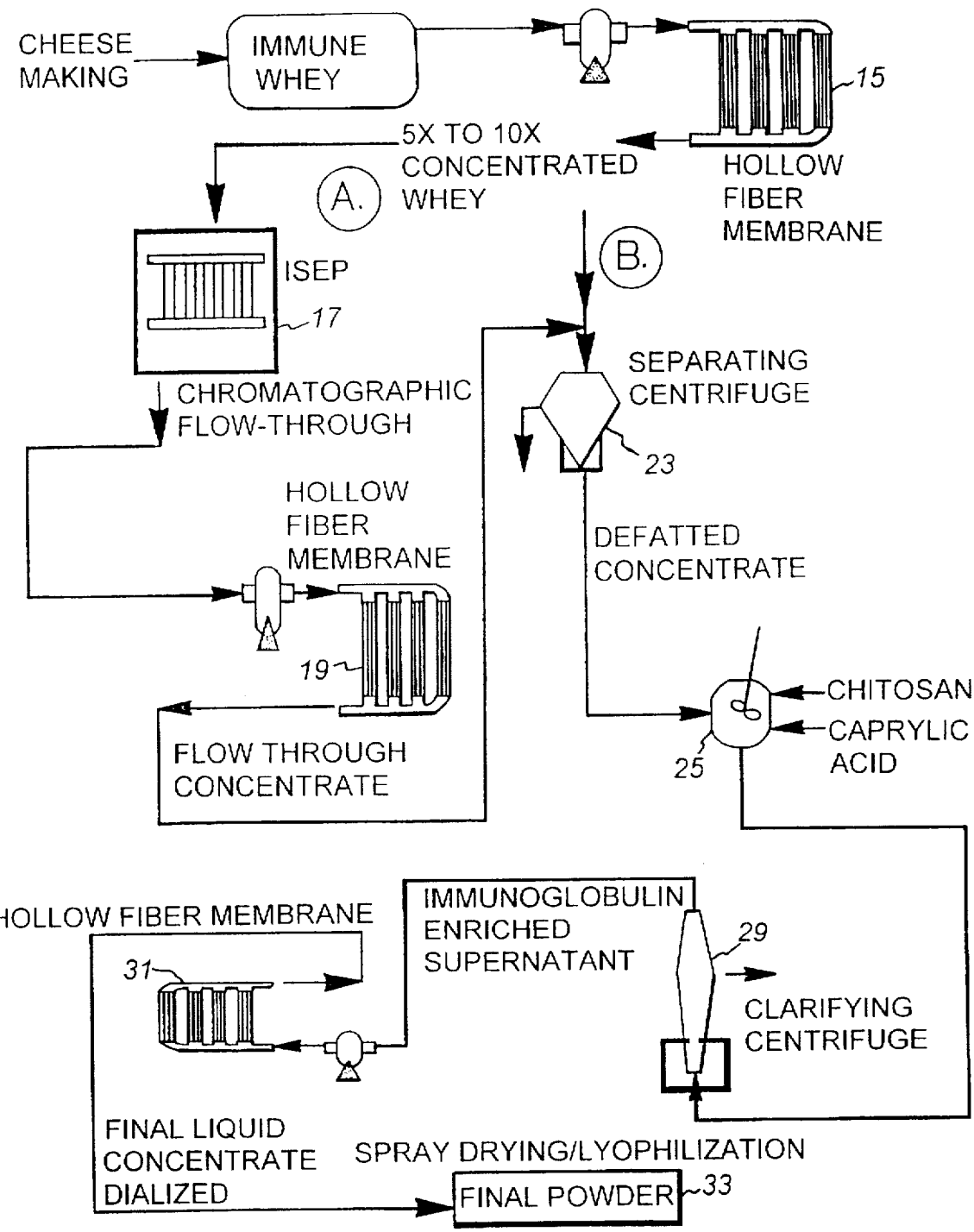
FIG. 1 depicts a flow diagram illustrating a method embodying features of the present invention.

The present invention will be described in detail as a method and apparatus for isolating immunoglobulins from whey. Reference will be made to FIG. 1 which illustrates features of the method in a flow diagram. Equipment for performing each step is well-known in the art.

As used herein, the term "whey" refers to the watery part of milk that separates from the curds, as in the process of making cheese. "Whey fractions" refers to a part of the whey comprising all or some of the whey proteins. "Partially deproteinized whey concentrate" refers to a part of the whey in which all or some of the nonimmunoglobulin proteins are removed. Embodiments of the present method and apparatus can be used to make an immunoglobulin product capable of being administered in a relatively small dosage form.

The process illustrated in FIG. 1 begins with cheese making, and the products of whey separation and clarification. The source of concentrated whey contains whey preferably produced from a swiss, cheddar, mozzarella or provolone cheese making process. The whey originates from milk produced by bovines which have been vaccinated with one or more antigens. Thus, such animals will secrete within their milk immunoglobulins that are directed to such antigen or antigens. Whey from one or more animals immunized with different antigens can be pooled to obtain immunoglobulins that are directed to a plurality of antigens.

Preferably, the whey is pasteurized. Typically pasteurization conditions comprise a temperature of 159°–161° F. for a period of time of 15–17 seconds. Preferably, the whey is concentrated by a factor of 5 to 10-fold over whey recovered is directly from cheese making processes. Preferably, the whey is concentrated by hollow fiber or spiral membrane ultrafiltration depicted generally by the numeral 15. A preferred ultrafiltration process has a molecular weight cutoff of about 30,000 Daltons.

A preferred ultrafiltration process utilizes polysulphone hollow fiber membranes.

During the ultrafiltration process, a feed-to-permeation ratio of 5 to 1 is typical with a lumen feed pressure of 25 to 40 psi, and an operating temperature of 10°–12° C.

Concentrated whey produced by ultrafiltration may be subjected to an optional ion exchange chromatography step, illustrated in FIG. 1 as pathway A. Preferably, the optional chromatography step comprises the removal of an amount of non-immunoglobulin proteins with an anionic exchange resin. This step is designated generally with the numeral 17. Following the anion exchange process, the flow-through comprises an immunoglobulin enriched fraction. Preferably, the IgG rich fraction is subjected to further ultrafiltration and further ion exchange chromatography to remove additional non-immunoglobulin proteins. The ultrafiltration step is designated generally with the numeral 19. These steps of ion exchange chromatography and ultrafiltration can be repeated as necessary.

The Ig fraction after final ion exchange chromatography and ultrafiltration is centrifuged for fat removal. The step of centrifugation may be performed on the concentrated whey product from an initial ultrafiltration step 15 as represented by pathway B. Preferably, a dairy separator is utilized at 3,000 to 12,000 rpm (5–15,000×g) and the centrifugation is performed at a temperature of 10° to 55° C. This step is generally designated by the numeral 23. The separated or delipidated whey constitutes a source of concentrated whey for the precipitation treatments which follow.

A cationic polymer is selected to cooperate with an intended fatty acid to undergo precipitation of lipids as the fatty acid reacts with proteins. Cationic polymers are preferably selected from the group comprising polypeptides or polysaccharides. A preferred polysaccharides is chitosan. A particularly preferred type of chitosan is SEACURE 443 brand chitosan (Pronova, Inc.), a partially deacetylated poly-N-acetylglucosamine derived from shrimp.

An amount of chitosan effective to form a precipitate of residual lipids upon imposition of precipitation conditions is approximately 0.2% by volume. The pH of this mixture is adjusted to between pH 4.5 and 5.0 by the addition of a NaOH solution. This pH adjusted mixture is then further reacted by the addition of a fatty acid preferably caprylic acid which reacts with proteins as the chitosan polymer reacts with lipids.

A preferred polypeptide is selected from the group consisting of basic polyamino acids or acid soluble basic proteins such as type A Gelatin (pI 7.0–9.0). These polypeptides are capable of forming a lipid precipitate at a pH between 4.5 and 5.0 at concentrations of 1–5% by weight polypeptide.

An effective amount of caprylic acid, to form a protein precipitate upon imposition of precipitation conditions is approximately 5% by weight volume. Mixing of chitosan, caprylic acid and concentrated whey may comprise the use of stirrers, paddles or other mixing apparatus known in the art. Lipid precipitation conditions for chitosans and lipids, comprise a temperature of 20° to 25° C. and a pH of 4.5 to 5.0. Protein precipitation conditions, for non-IgG proteins and caprylic acid, comprise a temperature of 20° to 25° C. and a pH of 4.5 to 5.0. Thus, lipid precipitation conditions and protein precipitation conditions may be imposed simultaneously.

Preferably, lipid precipitation conditions and protein precipitation conditions are imposed for 5 to 30 minutes after the admixture is formed by mixing. That is, a period of 5 to 30 minutes is allowed for the mixture to stand substantially motionless, with a 15 minute period preferred.

An appropriate centrifuge capable of receiving the admixture containing a lipid precipitate, and a protein precipitate is used to separate the solid and liquid phases. The centrifuge should be capable of subjecting the mixture to a force of 15–20,000×g and preferably an ejecting solid centrifuge. A preferred bowl centrifuge is a Sharples centrifuge and a preferred ejecting centrifuge is a Carr or Alpha Laval centrifuge. Preferably, the centrifuge assembly is maintained at a temperature of 20° to 25°. Under these conditions the centrifuge separates the lipid precipitate and protein precipitate from the immunoglobulin rich supernatant. The lipid precipitate, comprising lipid and chitosan, aids in the removal of the protein precipitate allowing low gravity forces to remove substantially all of the colloidal particles. Following centrifugation the pH of the liquid supernatant fraction is adjusted to 6.5.

The immunoglobulin rich supernatant is subjected to further concentration. This concentration is performed by ultrafiltration represented generally by the numeral 31. Preferably, ultrafiltration is performed using polysulphone hollow fiber membranes having a molecular weight cutoff of 20,000–150,000 Daltons and most preferably 30,000 Daltons. This ultrafiltration step can produce a further concentration of the supernatant by 15 to 25-fold. The ultrafiltration allows further permeation of low molecular weight polypeptides through the membranes while retaining an immunoglobulin rich retentate. Typically, the ultrafiltration has a feed-to-permeation ratio of 5:1, a lumen feed pressure of 15 to 30 psi, and is maintained at a temperature of 10°–12° C.

The immunoglobulin rich retentate can be further diafiltered using a polysulphone hollow fiber membrane having a nominal molecular weight cutoff of 20,000 to 150,000 Daltons or most preferably, 30,000 Daltons. The retentate is diafiltered utilizing a 15 mM potassium citrate buffer in soft water at a pH of 6.5. The diafiltration allows further permeation of polypeptides, minerals and lactose. Diafiltration is performed with a permeation ratio of 5:1, a lumen feed pressure of 15 to 30 psi, and a temperature of 10°–12° C.

A final retentate from the diafiltration is dried by either freeze drying or spray drying. This step is generally designated by the numeral 33 in FIG. 1. The dry powder is characterized as at least 85% protein, which protein represents 70% pure Ig, and less than 6% lipid by weight.

These and other features will be apparent from the following examples which further highlight important aspects of the present invention.

Example 1—This Example features the making of
an immunoglobulin product with activity against
enterotoxigenic *E. coli*

Hyperimmune milk was processed into provolone or mozzarella cheese by standard dairy practices. The aqueous whey fraction containing immunoglobulins was clarified and separated using standard dairy whey centrifugation methods. Clarified whey was first pasteurized by heating of 159° F. for 15 sec. using a standard dairy HTST pasteurizer. The heat treated whey was concentrated sixfold (6×) using hollow fiber membranes with a molecular weight cut off of 30,000 Daltons. Concentrated whey was enriched in immunoglobulins by anion exchange chromatography using an ISEP Chromatography System (Advanced Separation Technologies) in a process generally depicted as pathway A. See FIG. 1. Whey concentrate in this procedure is first adjusted to pH 6.8 by addition of a NaOH solution and passed over 10×100 cm columns containing a quaternary ammonium substituted polystyrene resin. Resin was first washed and pre-equilibrated to pH 7.0 with dilute buffer. Non-immunoglobulin proteins were absorbed under these conditions while the flow-through fraction was enriched in immunoglobulins.

The flow-through fraction was then concentrated by hollow fiber filtration (A/G Technology), using polysulfone filtration cassettes (30,000 MW cut off). The resulting flow-through concentrate was centrifuged to remove excess non-polar lipids.

Remaining phospholipids and residual non-Ig proteins were then precipitated by sequential addition of the flocculating agents chitosan (Pronova, Inc.) and caprylic acid. The precipitation reaction was carried-out using chromatographically deproteinized and defatted whey at a temperature of 20°–25° C. Chitosan was added to a final concentration of 0.2% and the pH of the mixture adjusted to pH 4.6. Caprylic acid was added to a final concentration of 5% by volume and the mixture stirred intermittently for 30 minutes.

The resulting precipitate was removed by centrifugation in a Sharples Centrifuge (Alfa Laval, Model AS-16) and the supernatant adjusted to pH 6.5 by the addition of NaOH. The centrifugation supernatant was concentrated to approximately 20% solids using a hollow fiber filtration system. After concentration, residual lactose, milk peptides and other salts were removed by step-wise diafiltration against three volumes of 15 mM potassium citrate pH 6.5.

The buffered immunoglobulin fraction was subsequently lyophilized to produce a final powder. Analysis of a representative lot of anti-E. coli immunoglobulin produced by this procedure revealed that the lyophilized powder contained 78% protein, 5.5% fat, 1.1% carbohydrate, 10.5% ash due to added potassium citrate buffer, 2.2% residual ash and 2.7% moisture. Ig comprised 79% of the total protein as revealed by scanning densitometry and SDS-polyacrylamide gel electrophoresis. Additional milk proteins present included beta-lactoglobulin, alpha-lactalbumin, serum albumin, and trace amounts of casein. Table 1 below describes the recovery of immunoglobulin activity and the Ig purity at different stages in this purification process.

TABLE 1

Summary of Anti-E. coli Immunoglobulin Product Purification

| Process Intermediate | Anti-E. coli Activity (U/ml) | Volume (L) | % Antibody Activity Recovery | % Ig/Total Protein |
| --- | --- | --- | --- | --- |
| Pasteurized Whey | 28 | 3800 | 100% | 1.57% |
| 6× Whey Concentrate | 160 | 633 | 95.3% | 2.29% |
| Chromatographic Flow Through | 108 | 783 | 79.8% | 8.85% |

TABLE 1-continued

Summary of Anti-E. coli Immunoglobulin Product Purification

| Process Intermediate | Anti-E. coli Activity (U/ml) | Volume (L) | % Antibody Activity Recovery | % Ig/Total Protein |
| --- | --- | --- | --- | --- |
| Defatted Concentrate | 1861 | 45.6 | 79.9% | 11% |
| Ig Concentrate | 4750 | 11.4 | 51.1% | 79% |

Example 2—Preparation of Anti-*Cryptosporidium parvum* Immunoglobulins

Hyperimmune milk from cows immunized with a killed *C. parvum* vaccine was processed into provolone or mozzarella cheeses by standard cheese making procedures. The aqueous whey fraction containing immunoglobulins was clarified and separated using standard whey centrifugation methods. The schematic for anti-Cryprosporidium immunoglobulin purification in this example is shown in FIG. 1.

Using pasteurization and hollow fiber ultrafiltration procedures described for initial immune whey processing in Example 1, a 6× whey concentrate was prepared and subjected to direct chitosan/caprylic treatment as outlined in FIG. 1 (pathway B). Chitosan was added to a final concentration of 0.15% by weight while stirring the whey concentrate. The pH of this mixture was adjusted to pH 4.9 by the addition of an NaOH solution after which caprylic acid was added to a final concentration of 4.0% by volume with mixing. The chitosan and caprylic precipitation reactions proceeded at 23° C. for 30 minutes with intermittent stirring.

The chitosan-lipid and caprylic-protein precipitates were separated by centrifugation in a Sorvall centrifuge at 10,000×g and the resulting supernatant adjusted to pH 6.5 by the addition of NaOH. Analysis of anti-Cryptosporidium antibody activity was carried out using standard sandwich ELISA procedures with *C. parvum* antigens coated on microtiter plates.

Ig purity at different steps was determined by densitometric scanning of 4–20% SDS-PAGE gels run under non-reducing conditions at pH 8.5 which were stained with Coomassie Blue. The results of this purification are shown in Table 2 below.

TABLE 2

Summary of Anti-*Cryptosporidium parvum* Immunoglobulin Purification

| Process Intermediate | Anti-Crypto Activity (U/ml) | % Antibody Activity Recovery | % Purity Ig/Total Protein |
| --- | --- | --- | --- |
| Ray Whey | 824 | 100 | 6.7 |
| Pasteurized Whey | 761 | 92.4 | 6.7 |
| 6× UF Whey Concentrate | 4611 | 100 | 8.2 |
| Chitosan/Caprylic Supernatant | 3476 | 75.5 | 66.7 |

Example 3—Preparation of Rotavirus Immunoglobulins

This Example describes making an Ig product for preventing or treating Rotavirus infections. Cows would be immunized with a vaccine containing killed virus or purified viral neutralization antigens (eg. G or P antigens) representing the four major rotavirus types (1–4) infective for humans. Hyperimmune milk would be processed into provolone or mozzarella cheese by standard dairy practices. The aqueous whey fraction containing immunoglobulins would be clarified and separated using standard dairy whey centrifugation methods. Clarified whey would be first pasteurized by heating of 159° F. for 15 sec. using a standard dairy HTST pasteurizer. The heat treated whey would be concentrated sixfold (6×) using hollow fiber membranes with a molecular weight cut off of 30,000 Daltons. Concentrated whey would be enriched in immunoglobulins by anion exchange chromatography using an ISEP Chromatography System (Advanced Separation Technologies) in a process generally depicted as pathway A of FIG. 1. Whey concentrate in this procedure would be first adjusted to pH 6.8 by addition of a NaOH solution and passed over 10×100 cm columns containing a quaternary ammonium substituted polystyrene resin. Resin would be first washed and pre-equilibrated to pH 7.0 with dilute buffer. Non-immunoglobulin proteins would be absorbed under these conditions while the flow-through fraction would be enriched in immunoglobulins. In the alternative, a process depicted in pathway B of FIG. 1, and described in Example 2 can be utilized.

The flow-through fraction would be then concentrated by hollow fiber filtration (A/G Technology), using polysulfone filtration cassettes (30,000 MW cut off). The resulting flow-through concentrate would be centrifuged to remove excess non-polar lipids.

Remaining phospholipids and residual non-Ig proteins would be precipitated by sequential addition of the flocculating agents chitosan (Pronova, Inc.) and caprylic acid. The precipitation reaction would be carried-out using chromatographically deproteinized and defatted whey at a temperature of 20°–25° C. Chitosan would be added to a final concentration of 0.2% and the pH of the mixture adjusted to pH 4.6. Caprylic acid would be added to a final concentration of 5% by volume and the mixture stirred intermittently for 30 minutes.

The resulting precipitate would be removed by centrifugation in a Sharples Centrifuge (Alfa Laval, Model AS-16) and the supernatant adjusted to pH 6.5 by the addition of NaOH. The centrifugation supernatant would be concentrated to approximately 20% solids using a hollow fiber filtration system. After concentration, residual lactose, milk peptides and other salts would be removed by step-wise diafiltration against three volumes of 15 mM potassium citrate pH 6.5.

The buffered immunoglobulin fraction would be subsequently lyophilized to produce a final powder. Such antibodies purified from whey by the procedures described can be incorporated into foods or drinks to prevent rotavirus infections in young children and older adults.

Example 4—Preparation of *Shigella flexneri* Immunoglobulin

This Example describes making an Ig product for preventing or treating *Shigella flexneri* infections. Cows are immunized with a vaccine containing killed bacteria or purified cell wall antigens together with inactivated Shigella toxins. Hyperimmune milk would be processed into provolone or mozzarella cheese by standard dairy practices. The aqueous whey fraction containing immunoglobulins would be clarified and separated using standard dairy whey centrifugation methods. Clarified whey would be first pasteurized by heating of 159° F. for 15 sec. using a standard dairy HTST pasteurizer. The heat treated whey would be concentrated sixfold (6×) using hollow fiber membranes with a molecular weight cut off of 30,000 Daltons. Defatted whey would be enriched in immunoglobulins by anion exchange chromatography using an ISEP Chromatography System (Advanced Separation Technologies) in a process generally depicted as pathway A of FIG. 1. Whey concentrate in this procedure would be first adjusted to pH 6.8 by addition of a NaOH solution and passed over 10×100 cm columns containing a quaternary ammonium substituted polystyrene resin. Resin would be first washed and pre-equilibrated to pH 7.0 with dilute buffer. Non-immunoglobulin proteins would be absorbed under these conditions while the flow-through fraction was enriched in immunoglobulins. In the alternative, pathway B—a process depicted as described in FIG. 1, and Example 2, can be utilized.

The flow-through fraction would be then concentrated by hollow fiber filtration (A/G Technology), using polysulfone filtration cassettes (30,000 MW cut off). The resulting flow-through concentrate would be centrifuged to remove excess non-polar lipids.

Remaining phospholipids and residual non-Ig proteins would be precipitated by sequential addition of the flocculating agents chitosan (Pronova, Inc.) and caprylic acid. The precipitation reaction would be carried-out using chromatographically deproteinized and defatted whey at a temperature of 20°–25° C. Chitosan would be added to a final concentration of 0.2% and the pH of the mixture adjusted to pH 4.6. Caprylic acid would be added to a final concentration of 5% by volume and the mixture stirred intermittently for 30 minutes.

The resulting precipitate would be removed by centrifugation in a Sharples Centrifuge (Alfa Laval, Model AS-16) and the supernatant adjusted to pH 6.5 by the addition of NaOH. The centrifugation supernatant would be concentrated to approximately 20% solids using a hollow fiber filtration system. After concentration, residual lactose, milk peptides and other salts would be removed by step-wise diafiltration against three volumes of 15 mM potassium citrate pH 6.5.

The buffered immunoglobulin fraction would be subsequently lyophilized to produce a final powder. Antibodies to these antigens which are present in whey can be purified by the procedures described and administered in food, drink or capsule/tabled from for the prevention of Shigella infections among susceptible or exposed individuals.

Example 5—Preparation of *Heliobacter pylori* Immunoglobulins

This Example describes making an Ig product for preventing or treating *Heliobacter pylori* infections. Cows would be immunized with purified antigens of *H. pylori* represented by presumed virulence factors such as urease, vacuolating cytoxins and flagella which are thought to be important in bacterial infection of gastric mucosa. Hyperimmune milk would be processed into provolone or mozzarella cheese by standard dairy practices. The aqueous whey fraction containing immunoglobulins would be clarified and separated using standard dairy whey centrifugation methods.

Clarified whey would be first pasteurized by heating of 159° F. for 15 sec. using a standard dairy HTST pasteurizer. The heat treated whey would be concentrated sixfold (6×) using hollow fiber membranes with a molecular weight cut off of 30,000 Daltons. Concentrated whey would be enriched in immunoglobulins by anion exchange chromatography using an ISEP Chromatography System (Advanced Separation Technologies) in a process generally depicted as pathway A of FIG. 1. Whey concentrate in this procedure would be first adjusted to pH 6.8 by addition of a NaOH solution and passed over 10×100 cm columns containing a quaternary ammonium substituted polystyrene resin. Resin would be first washed and pre-equilibrated to pH 7.0 with dilute buffer. Non-immunoglobulin proteins would be absorbed under these conditions while the flow-through fraction would be enriched in immunoglobulins. In the alternative, a process depicted as pathway B in FIG. 1, and described in Example 2, can be utilized.

The flow-through fraction would be concentrated by hollow fiber filtration (A/G Technology), using polysulfone filtration cassettes (30,000 MW cut off). The resulting flow-through concentrate would be centrifuged to remove excess non-polar lipids.

Remaining phospholipids and residual non-Ig proteins would be then precipitated by sequential addition of the flocculating agents chitosan (Pronova, Inc.) and caprylic acid. The precipitation reaction would be carried-out using chromatographically deproteinized and defatted whey at a temperature of 20°–25° C. Chitosan would be added to a final concentration of 0.2% and the pH of the mixture adjusted to pH 4.6. Caprylic acid would be added to a final concentration of 5% by volume and the mixture stirred intermittently for 30 minutes.

The resulting precipitate would be removed by centrifugation in a Sharples Centrifuge (Alfa Laval, Model AS-16) and the supernatant adjusted to pH 6.5 by the addition of NaOH. The centrifugation supernatant would be concentrated to approximately 20% solids using a hollow fiber filtration system. After concentration, residual lactose, milk peptides and other salts would be removed by step-wise diafiltration against three volumes of 15 mM potassium citrate pH 6.5.

The buffered immunoglobulin fraction would be subsequently lyophilized to produce a final powder. Antibodies to these antigens which are purified from whey by the procedures described can be incorporated into foods, drinks, tablets or capsules to prevent infection or spread of *H. pylori* infections.

Example 6—Preparation of *Clostridium Difficule* Immunoglogulins

This Example describes making an Ig product for preventing or treating *Clostridium difficule* infections. Cows would be immunized with inactive toxins A & B from *C. difficile* together with other cell wall antigens that could promote aggregation or colonic bacterial levels. Hyperimmune milk would be processed into provolone or mozzarella cheese by standard dairy practices. The aqueous whey fraction containing immunoglobulins would be clarified and separated using standard dairy whey centrifugation methods. Clarified whey would be first pasteurized by heating of 159° F. for 15 sec. using a standard dairy HTST pasteurizer. The heat treated whey would be concentrated sixfold (6×) using hollow fiber membranes with a molecular weight cut off of 30,000 Daltons. Concentrated whey would be enriched in immunoglobulins by anion exchange chromatography using an ISEP Chromatography System (Advanced Separation Technologies) in a process generally depicted as pathway A of FIG. 1. Whey concentrate in this procedure would be first adjusted to pH 6.8 by addition of a NaOH solution and passed over 10×100 cm columns containing a quaternary ammonium substituted polystyrene resin. Resin would be first washed and pre-equilibrated to pH 7.0 with dilute buffer. Non-immunoglobulin proteins would be absorbed under these conditions while the flow-through fraction would be enriched in immunoglobulins. In the alternative, a process depicted as pathway B of FIG. 1, and described in Example 2, can be utilized.

The flow-through fraction would be then concentrated by hollow fiber filtration (A/G Technology), using polysulfone filtration cassettes (30,000 MW cut off). The resulting flow-through concentrate would be centrifuged to remove excess non-polar lipids.

Remaining phospholipids and residual non-Ig proteins would be then precipitated by sequential addition of the flocculating agents chitosan (Pronova, Inc.) and caprylic acid. The precipitation reaction would be carried-out using chromatographically deproteinized and defatted whey at a temperature of 20°–25° C. Chitosan would be added to a final concentration of 0.2% and the pH of the mixture adjusted to pH 4.6.

Caprylic acid would be added to a final concentration of 5% by volume and the mixture stirred intermittently for 30 minutes.

The resulting precipitate would be removed by centrifugation in a Sharples is Centrifuge (Alfa Laval, Model AS-16) and the supernatant adjusted to pH 6.5 by the addition of NaOH. The centrifugation supernatant would be concentrated to approximately 20% solids using a hollow fiber filtration system. After concentration, residual lactose, milk peptides and other salts would be removed by step-wise diafiltration against three volumes of 15 mM potassium citrate pH 6.5.

The buffered immunoglobulin fraction would be subsequently lyophilized to produce a final powder. Antibodies to these antigens which are purified from whey by the procedures described can be incorporated into colon specific delivery formulations and administered to prevent colitis infections by *C. difficile* associated with prolonged oral administration of antibiotics.

Example 7—Preparation of *Vibrio Cholerae* Immunoglobulins

This Example describes making an Ig product for preventing or treating *Vibrio cholerae* infections. Cows would be immunized with inactivated cholera toxin (A & B subunit) or individual subunits as well as cell antigens such as lipopolysaccharides which are believed to impart immunity to intestinal infections. Hyperimmune milk would be processed into provolone or mozzarella cheese by standard dairy practices. The aqueous whey fraction containing immunoglobulins would be clarified and separated using standard dairy whey centrifugation methods. Clarified whey would be first pasteurized by heating of 159° F. for 15 sec. using a standard dairy HTST pasteurizer. The heat treated whey would be concentrated sixfold (6×) using hollow fiber membranes with a molecular weight cut off of 30,000 Daltons. Concentrated whey would be enriched in immunoglobulins by anion exchange chromatography using an ISEP Chromatography System (Advanced Separation Technologies) in a process generally depicted as pathway A of FIG. 1. Whey concentrate in this procedure is would be first adjusted to pH 6.8 by addition of a NaOH solution and passed over 10×100 cm columns containing a quaternary ammonium substituted polystyrene resin.

Resin would be first washed and pre-equilibrated to pH 7.0 with dilute buffer. Non-immunoglobulin proteins would be absorbed under these conditions while the flow-through fraction would be enriched in immunoglobulins. In the alternative, a process depicted as pathway B of FIG. 1, and described in Example 2, can be utilized.

The flow-through fraction would be concentrated by hollow fiber filtration (A/G Technology), using polysulfone filtration cassettes (30,000 MW cut off). The resulting flow-through concentrate would be centrifuged to remove excess non-polar lipids.

Remaining phospholipids and residual non-Ig proteins would be precipitated by sequential addition of the flocculating agents chitosan (Pronova, Inc.) and caprylic acid.

The precipitation reaction would be carried-out using chromatographically de-proteinized and defatted whey at a temperature of 20°–25° C. Chitosan would be added to a final concentration of 0.2% and the pH of the mixture adjusted to pH 4.6. Caprylic acid would be added to a final concentration of 5% by volume and the mixture stirred intermittently for 30 minutes.

The resulting precipitate would be removed by centrifugation in a Sharples Centrifuge (Alfa Laval, Model AS-16) and the supernatant adjusted to pH 6.5 by the addition of NaOH. The centrifugation supernatant would be concentrated to approximately 20% solids using a hollow fiber filtration system. After concentration, residual lactose, milk peptides and other salts would be removed by step-wise diafiltration against three volumes of 15 mM potassium citrate pH 6.5.

The buffered immunoglobulin fraction would be subsequently lyophilized to produce a final powder. Antibodies to these antigens which are purified from whey by the procedures described can be used in foods, drinks, or administered as tablets or capsules to prevent oral infections.

Example 8

This Example describes making an immunoglobulin product wherein the cationic polymer is a cationic fibrous cellulose. A cationic fibrous cellulose would be substituted for chitosan in Examples 1–7 to precipitate phospholipids. A preferred cationic fibrous cellulose is sold under the mark "DE-23" by Whatman, Inc. of New Jersey, USA.

Example 9

This Example describes making an immunoglobulin product wherein the fatty acid has the formula $CH_3$—$(CH_2)_n$—COOH wherein n is a whole integer from 4–5 and 7–10. Fatty acids, where n is a whole integer from 4–5 and 7–10, would be substituted for caprylic acid in Example 1–7 to precipitate non-Ig proteins.

The invention claimed is:

1. A method of isolating immunoglobulin from whey, concentrated whey or whey fractions derived from a milk-bearing mammal, the method comprising the following steps in order:

a) providing a sample comprising whey, whey concentrate or whey fractions;

b) forming an admixture comprising the sample of step a) and a cationic polymer, the concentration of the cationic polymer in the admixture being appropriate for lipid precipitation;

c) forming a second admixture comprising the admixture of step b) and a fatty acid, the concentration of the fatty acid in the second admixture being appropriate for precipitation of non-immunoglobulin proteins;

d) precipitating lipids and non-immunoglobulin proteins from the second admixture of step c) to form an immunoglobulin-rich supernatant and a lipid and non-immunoglobulin protein precipitate; and e) isolating the immunoglobulin-rich supernatant from the mixture of step d).

2. The method of claim 1 wherein said cationic polymer is selected from the group consisting of polypeptides and polysaccharides.

3. The method of claim 2 wherein said cationic polymer is chitosan.

4. The method of claim 1 wherein said fatty acid has the formula $CH_3$—$(CH_2)_n$—COOH wherein n is a whole integer from 4–10.

5. The method of claim 4 wherein said fatty acid is caprylic acid.

6. The method of claim 1 wherein said lipid and non-immunoglobulin protein precipitate are separated from said immunoglobulin-rich supernatant by centrifugation.

7. The method of claim 1 further comprising concentrating the immunoglobulin-rich supernatant by ultrafiltration with a membrane having a molecular weight cutoff of from about 20,000 to about 150,000 Daltons to remove polypeptides and lactose to form a retentate.

8. The method of claim 7 wherein said retentate is diafiltered to form a dialyzed immunoglobulin concentrate.

9. The method of claim 8 wherein said dialyzed immunoglobulin concentrate is freeze-dried or spray-dried to form a powder.

10. The method of claim 1 wherein the milk-bearing mammal is a cow or a goat.

11. The method of claim 1 wherein the milk-bearing mammal is pre-immunized with an antigen to stimulate production of immunoglobulin which binds specifically to the antigen.

12. A method for isolating immunoglobulin from whey, concentrated whey or whey fractions derived from a milk-bearing mammal, the method comprising the following steps in order:

a) providing a sample comprising whey, whey concentrate or whey fractions;

b) forming an admixture comprising the sample of step a) and chitosan, the concentration of the chitosan in the admixture being appropriate for lipid precipitation;

c) forming a second admixture comprising the admixture of step b) and caprylic acid, the concentration of the caprylic acid in the second admixture being appropriate for precipitation of non-immunoglobulin proteins;

d) precipitating lipids and non-immunoglobulin proteins from the second admixture of step c) to form an immunoglobulin-rich supernatant and a lipid and non-immunoglobulin protein precipitate; and e) isolating the immunoglobulin-rich supernatant from the mixture of step d).

13. The method of claim 12 wherein the milk-bearing mammal is a cow or a goat.

14. The method of claim 12 wherein the milk-bearing mammal is pre-immunized with an antigen to stimulate production of immunoglobulin which binds specifically to the antigen.

* * * * *